US008577438B2

(12) United States Patent
Kube et al.

(10) Patent No.: US 8,577,438 B2
(45) Date of Patent: Nov. 5, 2013

(54) SENSOR FOR IN-VIVO MEASUREMENTS

(75) Inventors: Oliver Kube, Worms (DE); Andrea Rittinghaus, Neckarsteinbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/333,153

(22) Filed: Dec. 21, 2011

(65) Prior Publication Data

US 2012/0184835 A1  Jul. 19, 2012

Related U.S. Application Data

(63) Continuation of application No. PCT/EP2010/003451, filed on Jun. 9, 2010.

(30) Foreign Application Priority Data

Jun. 23, 2009  (EP) .................................... 09008183

(51) Int. Cl.
*A61B 5/04*  (2006.01)

(52) U.S. Cl.
USPC .......................................... 600/373; 600/394

(58) Field of Classification Search
None
See application file for complete search history.

(56) References Cited

U.S. PATENT DOCUMENTS

| 5,390,671 | A |  | 2/1995 | Lord et al. | |
|---|---|---|---|---|---|
| 5,391,250 | A | * | 2/1995 | Cheney et al. | 156/268 |
| 5,482,473 | A | * | 1/1996 | Lord et al. | 439/67 |
| 5,779,665 | A | * | 7/1998 | Mastrototaro et al. | 604/506 |
| 6,645,360 | B1 | * | 11/2003 | Eisele et al. | 204/426 |
| 6,942,518 | B2 | * | 9/2005 | Liamos et al. | 439/495 |
| 6,965,791 | B1 |  | 11/2005 | Hitchcock et al. | |
| 7,381,184 | B2 |  | 6/2008 | Funderburk et al. | |

FOREIGN PATENT DOCUMENTS

| DE | 601 30 536 T2 | 6/2008 |
|---|---|---|
| EP | 0 876 823 | 11/1998 |
| WO | WO 01/58348 A3 | 8/2001 |

OTHER PUBLICATIONS

International Search Report of the International Searching Authority; PCT/EP2010/003451; Jul. 15, 2010.
International Preliminary Report on Patentability; PCT/EP2010/003451; Jan. 29, 2011.

\* cited by examiner

*Primary Examiner* — Michael Kahelin
*Assistant Examiner* — Mitchell Alter
(74) *Attorney, Agent, or Firm* — Bose McKinney & Evans LLP

(57) ABSTRACT

The invention relates to a sensor for in vivo measurements comprising a planar substrate, and a sensor shaft bearing several electrodes, and a sensor head for connecting the sensor, wherein the sensor head has metal surfaces as contact fields for contact making, which are connected to the electrodes by way of conductor paths. The sensor head protrudes laterally to the sensor shaft so that the contact fields are arranged laterally from the sensor shaft, whereas the conductor paths extend in parallel on the sensor head transversely to the longitudinal direction of the sensor shaft. Also disclosed is a system having a sensor as just described and a suitable plug connector therefor.

24 Claims, 5 Drawing Sheets

SENSOR FOR IN-VIVO MEASUREMENTS

RELATED APPLICATIONS

This application is a continuation application of International Application PCT/EP2010/003451, filed Jun. 9, 2010, which claims priority to EP09008183.7, filed Jun. 23, 2009, both of which are hereby incorporated herein by reference.

BACKGROUND

The invention relates to a sensor for in-vivo measurements. A sensor of this type is known from U.S. Pat. No. 5,390,671. Sensors of this type enable electrochemical measurement of analytes in a human or animal body, for example of glucose or lactate. For this purpose, an electrode system, which is arranged on a distal region of a substrate that is provided as a sensor shaft, is introduced into the body of a patient such that a transcutaneous measurement can be carried out by electrochemical means. This process is commonly called insertion of the sensor. Usually, the sensor shaft is punctured into the body of a patient by means of a slit cannula that can be pulled out of the body of the patient after the insertion is effected such that the sensor shaft bearing the electrodes remains in the body of the patient. After the insertion, a proximal region of the substrate projects from the body and forms a sensor head for connection of the sensor to a measuring device. The sensor head bears metallized surfaces with contact fields and is usually provided in the form of a plug-in part such that a coupling or socket with a matching slit can be plugged onto the plug-in part to allow the sensor to be connected to a measuring or analytical device. In this context, the arrangement of the contact fields defines the plugging direction in which a plug connector is plugged onto the sensor head in order to connect the sensor.

Like all medical devices, sensors for in-vivo measurement must meet the highest requirements with regard to their reliability. Moreover, the sensors should be as easy to handle as possible such that they can also be used by medical laymen in an ideal case. Moreover, the use of a sensor should be associated with as little pain for the patient as possible.

SUMMARY

The present invention provides a sensor in which the above requirements are better met.

In one exemplary sensor embodiment, the sensor head protrudes laterally from the sensor shaft such that the contact fields are arranged aside the sensor shaft. Advantageously, the plugging direction defined by the arrangement of the contact fields is crosswise to the longitudinal direction of the sensor shaft.

Therefore, a plug connection can be closed by means of a plugging motion that proceeds transverse to a puncturing channel generated by the cannula and along (substantially parallel to) the skin surface of a patient in order to connect the sensor to a measuring or analytical device. For example, a coupling part with a slit that matches the sensor head can be plugged onto the sensor head. However, it is feasible just as well to arrange the sensor head in a support part which, together with the sensor head, forms an electrical plug connector.

Therefore, in a sensor according to these teachings, there is no need for a force in longitudinal direction of the puncturing channel in order to connect the sensor to a measuring or analytical device. Accordingly, it is feasible to prevent risk of the cannula or the sensor being inadvertently pressed even more deeply into the body of a patient and unnecessary pain being caused by the application of a force that would be required to close a plug connection. Therefore, the use of a sensor according to this disclosure is advantageously associated with less pain for a patient.

Moreover, the connection of a sensor as taught herein to a measuring device is experienced by patients as being more comfortable for psychological reasons as well. The application of a force in the direction of puncturing of a sensor that is situated inside one's own body is instinctively felt to be threatening and therefore uncomfortable. This issue can be addressed with a sensor according to these teachings. As a result, patients who connect the sensor to a measuring device themselves experience no psychological reluctance and can therefore effect an error-free plug connection more easily. A sensor according to this disclosure therefore has the added advantage of delivering measuring results with increased reliability.

Another important advantage of the disclosed sensor is, in particular, that there is no need to bend the substrate in order to connect the sensor to a measuring device. By dispensing with bending forces during the contacting of the sensor, the reliability of the plug connection can also be increased and the structure of the coupling part receiving the plug-in part can be simplified.

The substrate of a sensor according to exemplary embodiments can be provided as pliable, for example by producing it by cutting it from a plastic sheet. A pliable substrate is advantageous in that the sensor that is situated in the body of a patient can adapt to the motions of said body. For this reason, when it is specified herein that the substrate of a sensor is flat or substantially flat, this refers to a new, unused sensor with no bending forces acting on its substrate. Likewise, specifying that the plug-in part defines a plugging direction that is at an acute angle with respect to the longitudinal direction of the cannula, also refers to a new, unused sensor in a state in which no forces are acting on it.

The sensor head of a sensor can be provided as a plug-in part. For connection of the sensor to a measuring device, the sensor head can then plugged into a slit of a socket or a coupler by a user and a plug connection can be closed by this means. However, the sensor head can just as well be connected to a plug-in part by a manufacturer, whereby the plug-in part is plugged together with a matching plug connector part by a user in order to connect the sensor.

In an unused sensor, the substrate is typically arranged to be upright in the slit of a cannula. The cannula is used to generate a puncturing channel in the body of a patient. The cannula can be removed following a puncture, whereby the substrate remains inserted in the puncturing channel. Following the insertion, the plugging direction defined by the sensor head, which is preferably provided as a plug-in part, is therefore in a state with no force acting on it transverse to the puncturing channel.

It is advantageous to use a flat substrate, which can be manufactured with little effort, for example by cutting it from a sheet of plastic. In a lateral view, i.e., with a viewing direction perpendicular onto the narrow sides of the substrate, the substrate then has the shape of a straight strip. A plug-in part formed by the substrate as sensor head can be provided inexpensively according to the principle of a plug-in card. For this purpose, metallized surfaces can be arranged as contact fields for contacting on the plug-in part and/or section of the substrate forming the plug-in part, and can be connected to one of the electrodes each by means of strip conductors.

Similar to a circuit board, the electrodes and contact fields can be arranged on a top side or bottom side of the substrate.

In this context, all electrodes and contact fields can be situated on a single side of the substrate which is then usually called the top side. However, it is feasible just as well that electrodes and/or contact fields are arranged on both the top side and on the bottom side. In this context, one contact field on the top side can be connected to one contact field on the bottom side in an electrically conductive manner in order to improve the contacting. However, it is feasible just as well that the contact fields on the top side and bottom side each are connected to different electrodes such that the utilization of both the top side and the bottom side allows a particularly compact design to be implemented.

The sensor head can be designed to be elongate in shape and the longitudinal direction of the sensor head can be provided to be transverse to the longitudinal direction of the sensor shaft. The sensor head may also be wider than the sensor shaft.

The sensor head can extend perpendicular to the longitudinal direction of the sensor shaft such that the strip conductors on the sensor head extend perpendicular to the longitudinal direction of the sensor shaft. By this means, a plug-in part can be formed that defines a plugging direction that extends perpendicular to the longitudinal direction of the sensor shaft. However, sensors for in-vivo measurements are usually not punctured into the body of a patient perpendicular to the skin surface, but rather at an oblique angle. Therefore, the sensor head preferably extends at an oblique angle with respect to the longitudinal direction of the sensor shaft and defines a plugging direction that extends at an oblique angle with respect to the longitudinal direction of the sensor shaft. For this purpose, it is advantageous for the strip conductors on the sensor head to extend at an oblique angle with respect to the longitudinal direction of the sensor shaft. When the sensor is punctured into the body of a patient at an oblique angle with respect to the skin surface, the plug connection can then be closed in an ergonomically advantageous manner in that a plug connector for contacting the sensor head is moved approximately parallel to the skin surface.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DETAILED DESCRIPTION

Figure 1:
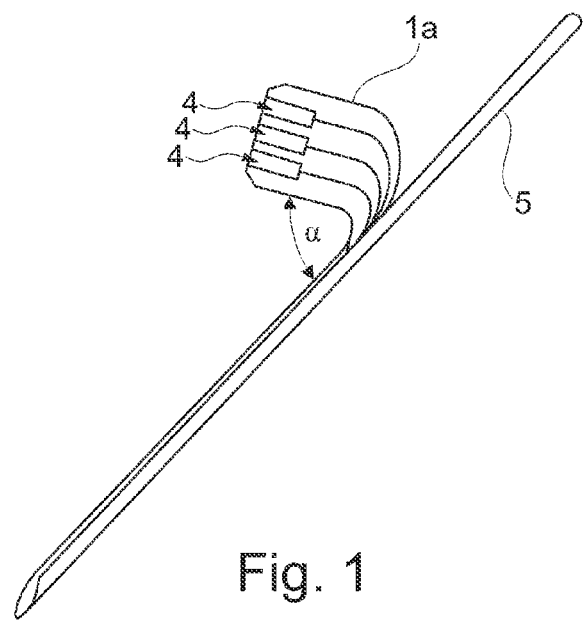
FIG. 1 shows a sensor according to the present disclosure.
Figure 2:
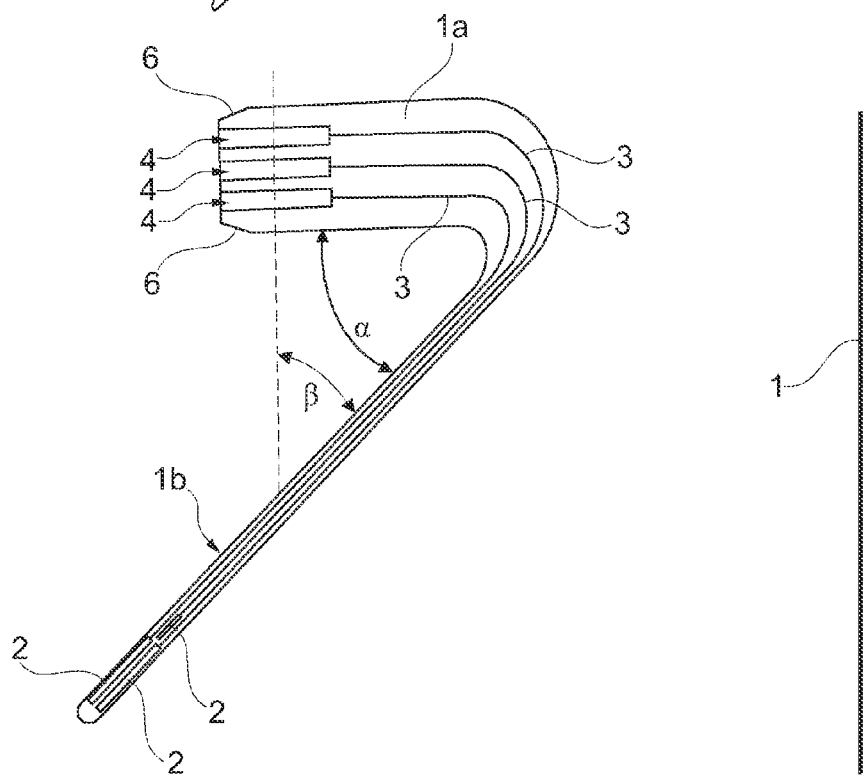
FIG. 2 shows the sensor shown in FIG. 1 with the cannula being absent.

The embodiments described below are not intended to be exhaustive or to limit the invention to the precise forms disclosed in the following detailed description. Rather, the embodiments are chosen and described so that others skilled in the art may appreciate and understand the principles and practices of these teachings.

The sensor for in-vivo measurements shown in FIGS. 1 to 4 has a flat substrate 1 that forms a sensor head 1a and a sensor shaft 1b that originates on the sensor head 1a. The sensor shaft 1b bears electrodes 2 for electrochemical measurements which each are connected through strip conductors 3 to contact fields 4 that are arranged on the sensor head 1a.

Figure 3:
FIG. 3 shows a lateral view with respect to FIG. 2.
Figure 4:
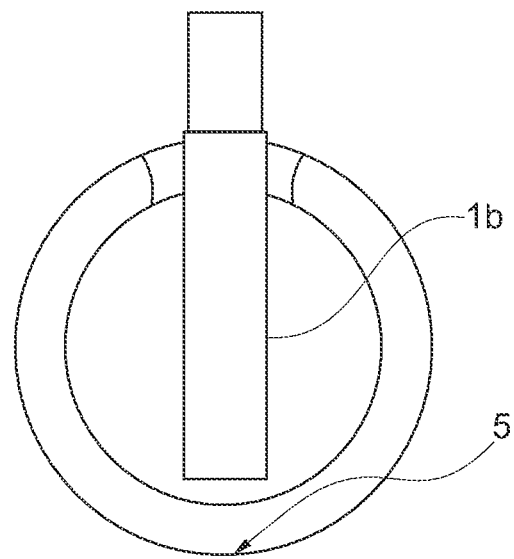
FIG. 4 shows a cross-sectional view with respect to FIG. 1.

The substrate 1 is planar. Therefore, the sensor shaft 1b and the sensor head 1a have a coplanar surface, or two co-planar surfaces to be more precise, namely the top side and the bottom side of the substrate 1, since the substrate 1 was cut from a sheet of plastic. In a lateral view, i.e. with a viewing direction perpendicular onto the narrow sides of the sensor, the sensor therefore appears as a straight strip as is shown in FIG. 3.

The sensor head 1a sticks out from the sensor shaft 1b on the side such that the contact fields 4 are arranged lateral to the sensor shaft 1b and the strip conductors 3 on the sensor head 1a extend next to each other transverse to the longitudinal direction of the sensor shaft 1b.

In order to connect the sensor to a measuring device, the sensor head 1a with the contact fields 4 can be plugged into a matching socket. Advantageously, due to the arrangement of the contact fields 4, the plugging motion that is thus required proceeds transverse with respect to the longitudinal direction of the sensor shaft 1b. A motion of said type is easy to perform by a user. It allows, in particular, any risk of the sensor being pressed more deeply into the body and unnecessary pain being caused thereby to be prevented.

If the substrate is thin and therefore flexible, plugging a socket onto the sensor head 1a may be difficult for some users. As a remedy, the manufacturer can arrange the sensor head 1a in a support part, which, together with the sensor head 1a, forms an electrical plug connector whose connecting direction, i.e. the plugging direction, in which a matching plug connector needs to be moved in order to connect it, extends transverse with respect to the longitudinal direction of the sensor shaft 1b. An embodiment example of a sensor having a support part 7 of this type is shown in a lateral view in FIG. 7 and in a sectional view in FIG. 8. FIG. 9, in addition, shows a plug connector 9 that matches the plug connector formed by the support part 7 and the sensor head 1a, and, together with the sensor, forms a system. The plug connector 9 has spring-actuated mobile line contacts 10 that extend in the plugging direction and contact one of the contact fields 4 of the sensor each when the plug connection is closed. The sensor head 1a can form a plug connector on its own or in conjunction with a support part 7.

Accordingly, regardless of the presence or absence of a support part, the sensor head 1a can be electrically connected to a measuring device by means of a plug connection. In this context, the contact fields are arranged on the sensor head in such a manner to ensure that a plug connector for connecting the sensor to a measuring device can be plugged onto the sensor shaft 1b only by means of a plugging motion that proceeds transverse with respect to the longitudinal direction.

The plugging direction defined by the arrangement of the contact fields 4 on the sensor head 1a forms an angle $\alpha$ with respect to the longitudinal direction of the sensor shaft 1b. The contact fields 4 are arranged next to each other in a row on the plug part 1a. The plugging direction is transverse to the direction of the row. The row of contact fields 4 forms an angle $\beta$ that is drawn in FIG. 2 with respect to the longitudinal direction of the strip-shaped sensor shaft 1b.

Figure 6:
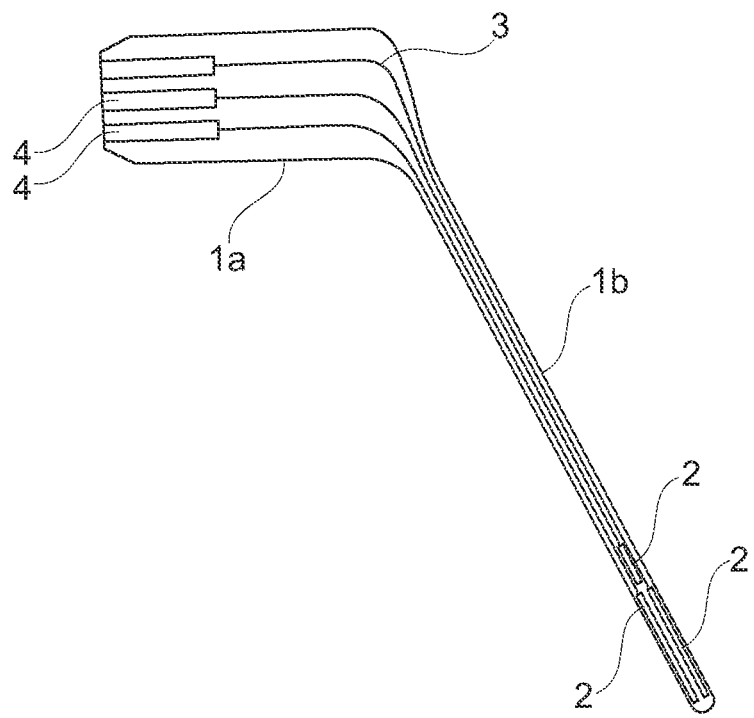
FIG. 6 shows another embodiment of a sensor according to the present disclosure.

In the embodiment shown, the angle α deviates by 20° to 70°, in particular by 30° to 60°, from a right angle; i.e. it is 20° to 70°, in particular 30° to 60°, in the case of an acute angle or it is 110° to 160°, in particular 120° to 150° in the case of an obtuse angle. In the embodiment shown, the angle α is an acute angle. However, the sensor head 1a can also protrude from the sensor shaft 1b on the opposite side, as is shown in FIG. 6. In this case, the angle α is an obtuse angle. The angle β also deviates by 20° to 70°, for example 30° to 60°, from a right angle in the embodiments examples shown.

Figure 7:
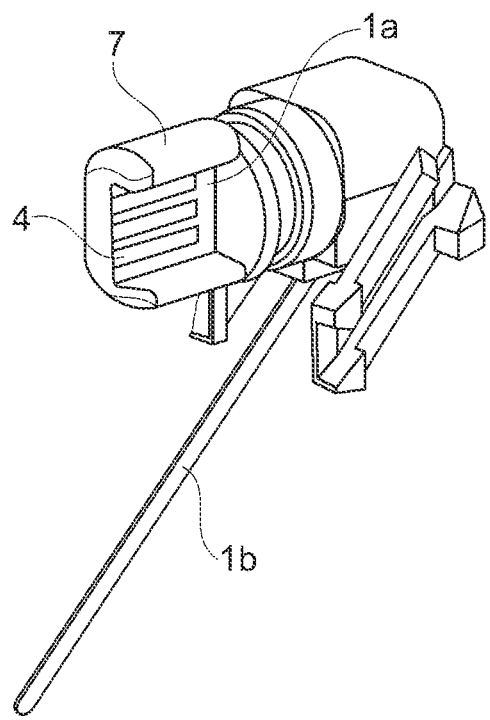
FIG. 7 shows the embodiment shown in FIG. 2 having a support part.
Figure 8:
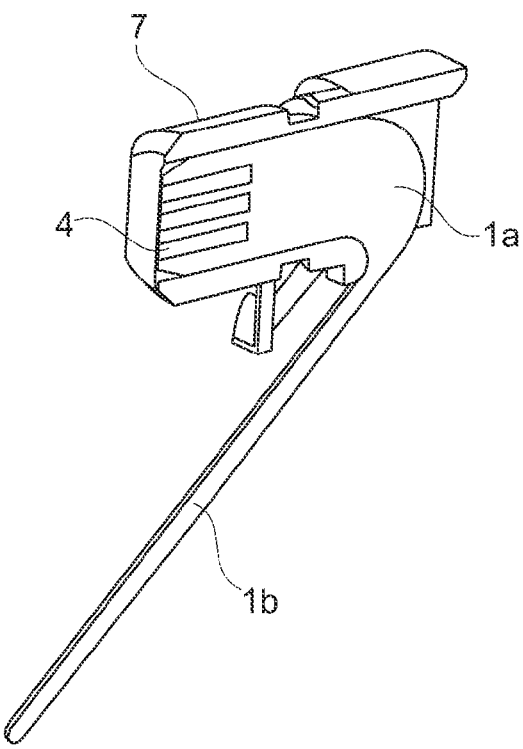
FIG. 8 shows a sectional view with respect to FIG. 7.
Figure 9:
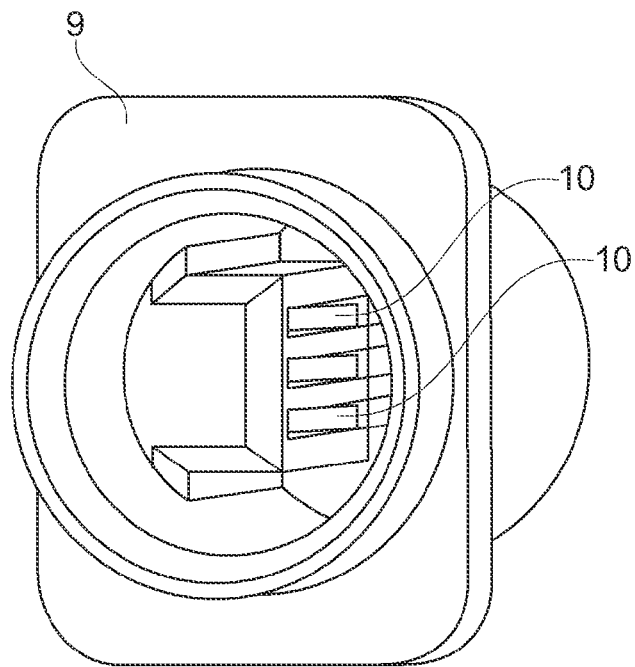
FIG. 9 shows a plug connector for the embodiment shown in FIG. 7.

The sensor head 1a has lateral lead-in chamfers 6 that simplify for a user the process of plugging-on a coupling part that is not shown here or simplify the plugging-on of a support part 7 shown in FIGS. 7 and 8 during manufacture. Said lead-in chamfers 6 are arranged on opposite side edges of the sensor head 1a. Due to the lead-in chamfers 6, the width of the sensor head 1a decreases towards the front end onto which a plug connector is plugged in order to connect the sensor.

The substrate 1 can be coated with metal much like a circuit board in order to provide strip conductors 3 and contact fields 4. The contact fields 4 are preferably provided to be elongate and extend transverse with respect to the longitudinal direction of the sensor shaft 1b such that the longitudinal direction of the contact fields coincides with the plugging direction in the embodiment shown. Advantageously, the reliability of an electrical contact that is established by means of the contact fields 4 can thus be increased.

In the embodiment shown, a working electrode, a counter-electrode, and a reference electrode are present, whereby there is no absolute need to have a reference electrode present. Said electrodes 2 are arranged on the same side of the substrate in the embodiment shown. However, as a general rule, it is feasible just as well to arrange one or more electrode(s) on the opposite side of the substrate, i.e. its rear side, for example in order to implement a particularly compact design. However, the rear side of the substrate can just as well be utilized to arrange further electrodes there. Apart from this, it is feasible just as well to arrange multiple working electrodes on one side of the substrate 1. This allows a sensor to be generated that has measuring sensitivities that are matched to different concentration ranges or can be used for measurements on different analytes.

The electrodes 2 are schematically shown to be rectangular in the figures, but can in fact be of any shape.

The substrate 1 can be manufactured inexpensively from plastic material, for example by cutting it from a sheet. For this reason, the substrate 1 is planar and has a rectangular cross-section as is evident from the lateral view shown in FIG. 3. In the embodiment shown, the sensor head 1a and the sensor shaft 1b have the same thickness. However, it is feasible just as well to provide the sensor head 1a and/or a part of the sensor shaft 1b that is adjacent to the sensor head 1a to be somewhat thicker than the part of the sensor shaft bearing the electrodes 2. By this means, the stability of the sensor can be increased such that a plug connection can be closed more easily even in the absence of a support part 7 surrounding the sensor head 1a.

The sensor head 1a can advantageously be provided to be elongate in shape in order to make it easier to plug-on a coupling part in order to connect the sensor to a measuring or analytical device or to plug-on a support part 7. In the embodiments shown, the sensor head 1a and the sensor shaft 1b, which extends straight, form the angle α.

The sensor includes a cannula 5 that can be used to insert the electrode system that is arranged on the sensor shaft 1b into the body of a patient for transcutaneous measurements. The cannula 5 has a slit that extends along its longitudinal direction and in which the sensor shaft 1b is arranged to be upright. As is shown, in particular, in FIG. 4, the sensor shaft 1b of the embodiment shown has a width that is larger than the internal diameter of the cannula 5 such that the sensor shaft 1b protrudes from the slit. However, it is feasible just as well for the width of the sensor shaft 1b to be smaller than the diameter of the cannula.

Since the substrate 1 is arranged to be upright in the slit, one narrow side of the substrate 1 faces the internal surface of the cannula that is situated opposite from the slit on the inside of the cannula 5. The opposite narrow side of the substrate 1, i.e. of the sensor shaft 1b that is provided in the form of a strip to be more specific, faces away from the cannula 5.

Figure 5:
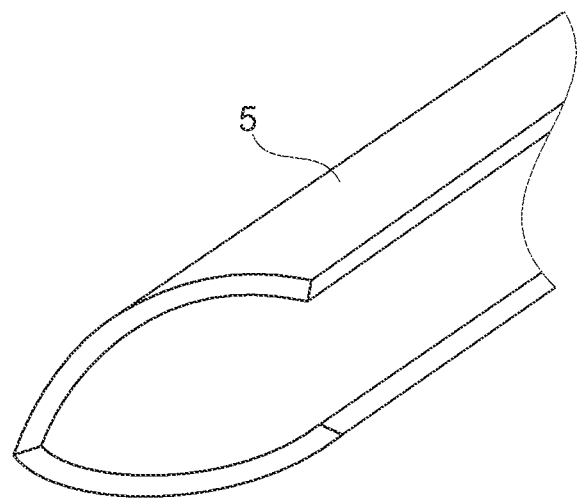
FIG. 5 shows a view of the tip of the cannula.

FIG. 5 shows the distal end of the cannula 5. As shown in the figure, the cannula 5 has a slanted end that ends in a tip. In this context, the slit is arranged on the side of the cannula that is opposite from the side comprising the tip.

Figure 10:
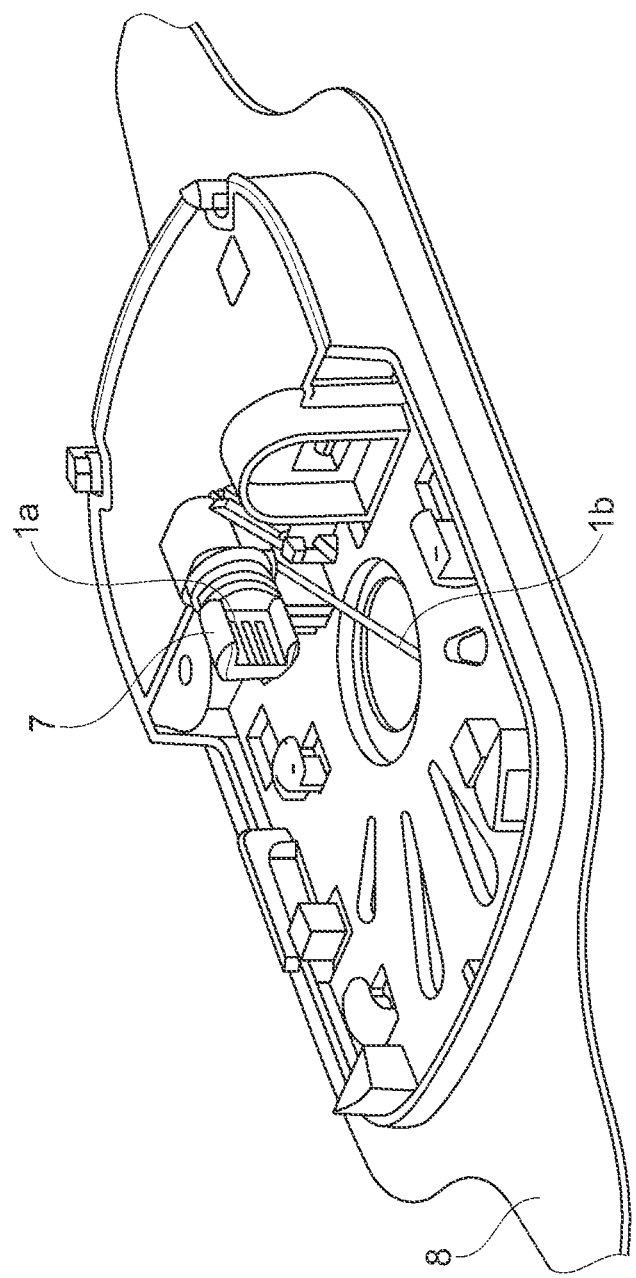
FIG. 10 shows the embodiment shown in FIG. 7 together with a carrier unit.

In use, the sensor can be secured to a carrier unit 8 that is glued to the body of a patient. An example of a carrier unit 8 of this type is shown in FIG. 10. Advantageously, a measuring unit supplying electrical current to the sensor by means of a plug connection can also be secured on a carrier unit of this type.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMBERS

1 Substrate
1a Sensor head
1b Sensor shaft
2 Electrode
3 Strip conductor
4 Contact field
5 Cannula
6 Lead-in chamfer
7 Support part
8 Carrier unit
9 Plug connector
10 Line contacts

What is claimed is:

1. A sensor for in-vivo measurements, comprising:
a substantially planar substrate, the substrate comprising a sensor shaft having multiple electrodes, a sensor head that is to be connected to a first electrical plug connector, the sensor head having metallized contact fields, and strip conductors connecting the contact fields to the electrodes, wherein, when there are no bending forces acting on the substrate in an unused sensor, the sensor head laterally protrudes from the sensor shaft such that the contact fields are arranged aside the sensor shaft; and
a support part in which the sensor head is arranged, the support part and sensor head together forming a second electrical plug connector, wherein the first electrical plug connector is connectable to the second electrical plug connector in a connecting direction, the connecting direction extending crosswise to the longitudinal direction of the sensor shaft, wherein the longitudinal direcion of the sensor shaft extends along the substrate from the electrodes to the sensor head.

2. The sensor of claim 1, wherein portions of the strip conductors located next to each other on the sensor head extend transverse to the longitudinal direction of the sensor shaft.

3. The sensor of claim 1, wherein the sensor head comprises lead-in chamfers.

4. The sensor of claim 1, wherein the sensor head and the longitudinal direction of the sensor shaft form an angle ($\alpha$) that deviates from a right angle by 20° to 70°.

5. The sensor of claim 1, wherein the sensor head and the longitudinal direction of the sensor shaft form an angle ($\alpha$) that deviates from a right angle by 30° to 60°.

6. The sensor of claim 1, wherein the sensor head and the longitudinal direction of the sensor shaft form an acute angle ($\alpha$).

7. The sensor of claim 1, wherein the contact fields are elongate and run transverse to the longitudinal direction of the sensor shaft.

8. The sensor of claim 1, wherein the contact fields are arranged next to each other in a row, whereby the row and the longitudinal direction of the sensor shaft form an angle ($\beta$) that deviates from a right angle by 20° to 70°.

9. The sensor of claim 1, wherein the contact fields are arranged next to each other in a row, whereby the row and the longitudinal direction of the sensor shaft form an angle ($\beta$) that deviates from a right angle by 30° to 60°.

10. The sensor of claim 1, wherein the sensor shaft comprises a strip whose width is larger than the thickness of the substrate.

11. The sensor of claim 1, wherein the sensor head is elongate and has its longitudinal direction oriented crosswise to the sensor shaft.

12. The sensor of claim 1, wherein the substrate comprises a sheet of plastic.

13. The sensor of claim 1, wherein the electrodes are arranged on a top side and/or a bottom side of the substrate.

14. The sensor of claim 1, wherein the substrate is positioned in a cannula having a slit.

15. The sensor of claim 14, wherein the cannula has a slanted end that ends in a tip, whereby the slit is arranged on the cannula's side that is opposite from the side comprising the tip.

16. The sensor of claim 1, wherein the connecting direction and the longitudinal direction of the sensor shaft form an angle ($\alpha$) that deviates from a right angle by 30° to 60°.

17. The sensor of claim 1, wherein the connecting direction is perpendicular to the sensor shaft and parallel to the geometric plane defined by the substrate.

18. The sensor of claim 1, wherein the connecting direction extends at an oblique angle with respect to the longitudinal direction of the sensor shaft.

19. A sensor system for in-vivo measurements, comprising:

a substantially planar substrate, the substrate comprising a sensor shaft having multiple electrodes, a sensor head having metallized contact fields, and strip conductors connecting the contact fields to the electrodes, wherein, when there are no bending forces acting on the substrate in an unused sensor, the sensor head laterally protrudes from the sensor shaft such that the contact fields are arranged aside the sensor shaft; and a support part in which the sensor head is arranged, the support part and sensor head together forming a first electrical plug connector; and a second electrical plug connector connectable to the first electrical plug connector in a connecting direction, the connecting direction extending crosswise to the longitudinal direction of the sensor shaft, wherein the longitudinal direction of the sensor shaft extends along the substrate from the electrodes to the sensor head.

20. The sensor system of claim 19, further comprising a cannula having a slit in which the sensor shaft can be removably arranged.

21. The sensor system of claim 19, wherein the second electrical plug has metallized contact parts which electrically connect to the metallized contact fields of the sensor head when the first and second electrical plug connectors are connected.

22. The sensor system of claim 19, wherein the connecting direction and the longitudinal direction of the sensor shaft form an angle ($\alpha$) that deviates from a right angle by 20° to 70°.

23. The sensor of claim 19, wherein the connecting direction is perpendicular to the sensor shaft and parallel to the geometric plane defined by the substrate.

24. The sensor of claim 19, wherein the connecting direction extends at an oblique angle with respect to the longitudinal direction of the sensor shaft.

* * * * *